United States Patent

Tanabe et al.

Patent Number: 5,814,513
Date of Patent: Sep. 29, 1998

[54] METHOD OF REMOVING CELLS FROM FERMENTATION BROTH THROUGH MEMBRANE

[75] Inventors: Toshiya Tanabe; Tohru Nakamura, both of Kawaski, Japan

[73] Assignee: Ajinomoto Co., Inc., Tokyo, Japan

[21] Appl. No.: 732,116

[22] Filed: Oct. 15, 1996

[30] Foreign Application Priority Data

Oct. 13, 1995 [JP] Japan .................................. 7-265275

[51] Int. Cl.$^6$ ....................................................... C12N 1/02
[52] U.S. Cl. .............................................................. 435/261
[58] Field of Search ............................................. 435/261

[56] References Cited

U.S. PATENT DOCUMENTS 5,665,869   9/1997   Ryland et al. .......................... 530/412

FOREIGN PATENT DOCUMENTS

| 0 184 882 | 6/1986 | European Pat. Off. . |
| 2 552674 | 4/1985 | France . |
| 2557873 | 7/1985 | France . |
| 33 26 888 | 2/1985 | Germany . |
| 3400603 | 7/1985 | Germany . |
| 2152031 | 7/1985 | United Kingdom . |

*Primary Examiner*—Jean C. Witz
*Attorney, Agent, or Firm*—Oblon, Spivak, McClelland, Maier & Neustadt, P.C.

[57] ABSTRACT

A method for removing cells from a fermentation broth obtained by culturing a microorganism belonging to the genus Escherichia through a membrane to separate the cells, comprising adding polyethyleneimine to the fermentation broth to form a mixture, and then filtering the mixture through the membrane to separate the cells, said method resulting in improving the membrane permeation rate compared to when no polyethyleneimine is added.

8 Claims, 2 Drawing Sheets

METHOD OF REMOVING CELLS FROM FERMENTATION BROTH THROUGH MEMBRANE

BACKGROUND OF THE INVENTION

1. Field of the Invention

The present invention relates to a method for removing cells, cell debris or dissolved high-molecular impurities through a membrane in the treatment of a fermentation broth obtained by culturing a microorganism belonging to the genus Escherichia, in which the membrane permeation rate is improved through pre-treatment under mild conditions. That is, the present invention relates to a method in which membrane fouling substances are preliminarily treated, and the membrane permeation rate is improved when removing cells through the membrane, thereby shortening the treatment time and minimizing the size of the equipment.

2. Description of the Background

In recent years, the technology of fermentative production using recombinant strains has advanced, and *Escherichia coli* (hereinafter abbreviated as "*E. coli*") which can easily be subjected to genetic manipulation has been often used for this purpose. When a desired product has been excreted outside of cells at the end of the fermentation, cells are usually removed by membrane separation or centrifugation after sterilization, and the resulting cell-free solution is subjected to a subsequent treatment step. When a desired product is present inside of cells, the cells are milled through freezing or using a homogenizer, a mill or the like, and then the cells and the cell debris are removed by membrane separation or centrifugation.

In general, the membrane separation can completely remove the cells to obtain a clear cell-free solution in comparison to the centrifugation. However, in cases where the permeation rate is low in the membrane separation, a large-sized device is required. A membrane for removing cells is generally a microfiltration membrane (hereinafter abbreviated as "MF"), an ultrafiltration membrane (hereinafter abbreviated as "UF") or the like. However, in the case of a fermentation broth obtained by culturing *E. coli* strains (hereinafter referred to as "an *E. coli* fermentation broth"), these membranes are problematic in that the permeation rate is low regardless of the milling.

It is known that heating of the fermentation broth is effective as a pre-treatment for improving the permeation rate in removing cells from a fermentation broth through a membrane. For example, Japanese Laid-Open Patent Application (Kokai) No. 91,196/1982 describes that when cells and high-molecular substances are separated through an ultrafiltration membrane, the membrane permeation rate is improved by heat-treating an inosine or guanosine fermentation broth with a pH of from 5.5 to 9.0 at from 90° to 110° C. Further, Japanese Laid-Open Patent Application (Kokai) No. 78,588/1985 describes that an ultrafiltration membrane permeation rate is improved by heating an amino acid fermentation broth at from 50° to 100° C.

However, as above mentioned, in cases of removing cells from an *E. coli* fermentation broth through a membrane, the permeation rate is extremely low, requiring a large-scaled membrane treatment equipment. It is also possible to improve the permeation rate by the above-mentioned method comprising pH adjustment and heat-treatment of the *E. coli* fermentation broth. However, so far as the *E. coli* fermentation broth is concerned, this method is not so effective. Further, the heat-treatment may cause coloration of the fermentation broth or formation of small amounts of by-product impurities. Still further, when a desired product is thermally unstable, this method cannot be applied thereto.

Accordingly, the development of a method for improving the membrane permeation rate through pre-treatment under milder conditions in the separation of cells from a fermentation broth obtained by culturing a microorganisms belonging to the genus Escherichia has been in demand.

SUMMARY OF THE INVENTION

The present invention relates to a method for removing cells, cell debris or dissolved high-molecular impurities from a fermentation broth obtained by culturing a microorganism belonging to the genus Escherichia through a membrane to separate the cells, comprising adding polyethyleneimine (hereinafter abbreviated as "PEI") to the fermentation broth to form a mixture, and then filtering the mixture through the membrane to separate the cells.

As stated above, in accordance with the method of the present invention, the membrane permeation rate of the fermentation broth can be improved without using large-scaled equipment. Further, it is also possible to increase the efficiency of the process for removal of cells from the fermentation broth using the membrane and to minimize the size of a membrane separation equipment for removal of cells.

BRIEF DESCRIPTION OF THE DRAWING

FIG. 2 is a graph showing a relationship between a change in the membrane permeation rate in MF filtration of a leucine fermentation broth over the course of time and an amount of PEI added.

DETAILED DESCRIPTION OF THE INVENTION

Figure 1:
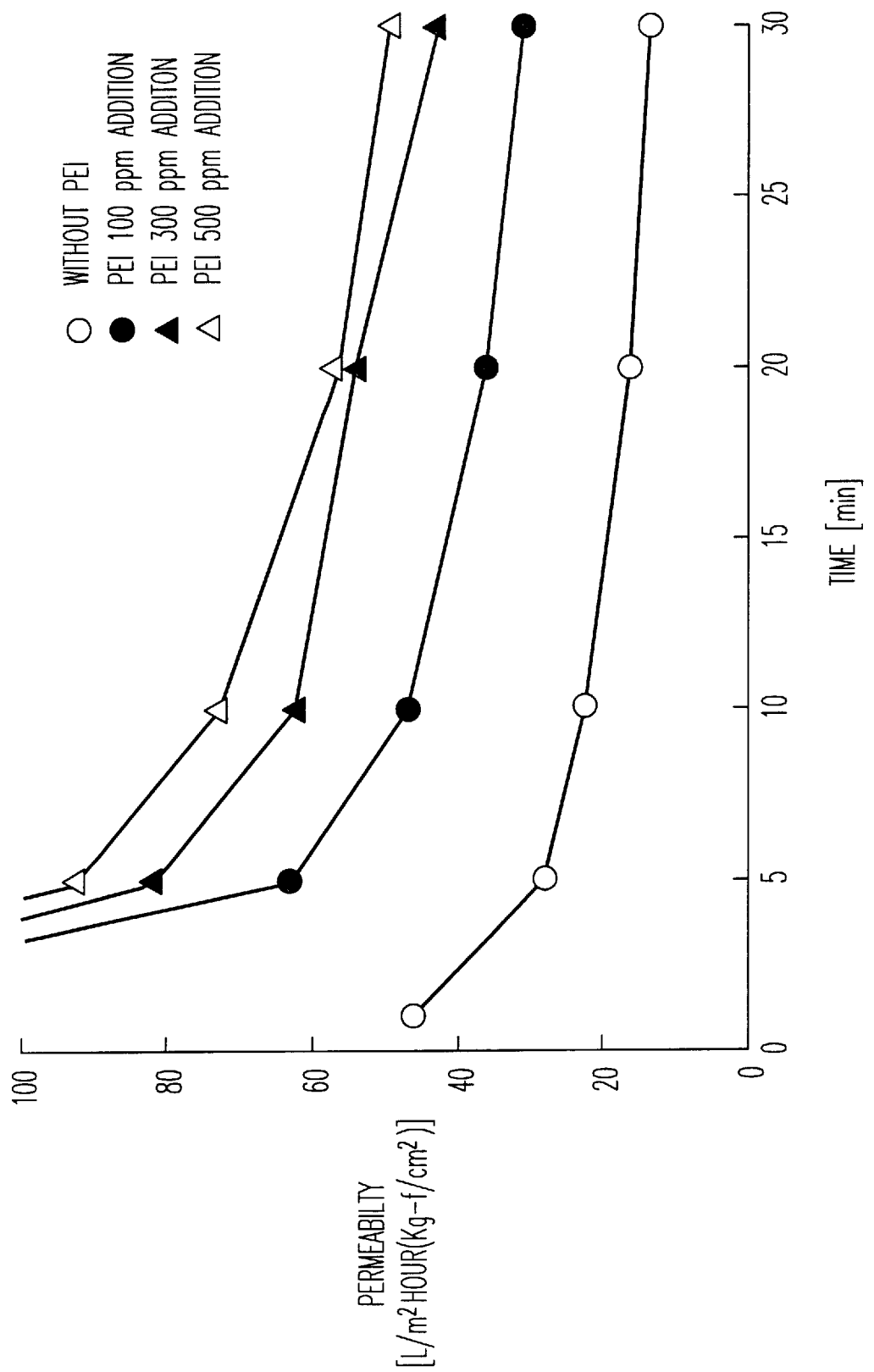
FIG. 1 is a graph showing a relationship between a change in the membrane permeation rate in UF filtration of a lysine fermentation broth over the course of time and an amount of PEI added.
Figure 1A:
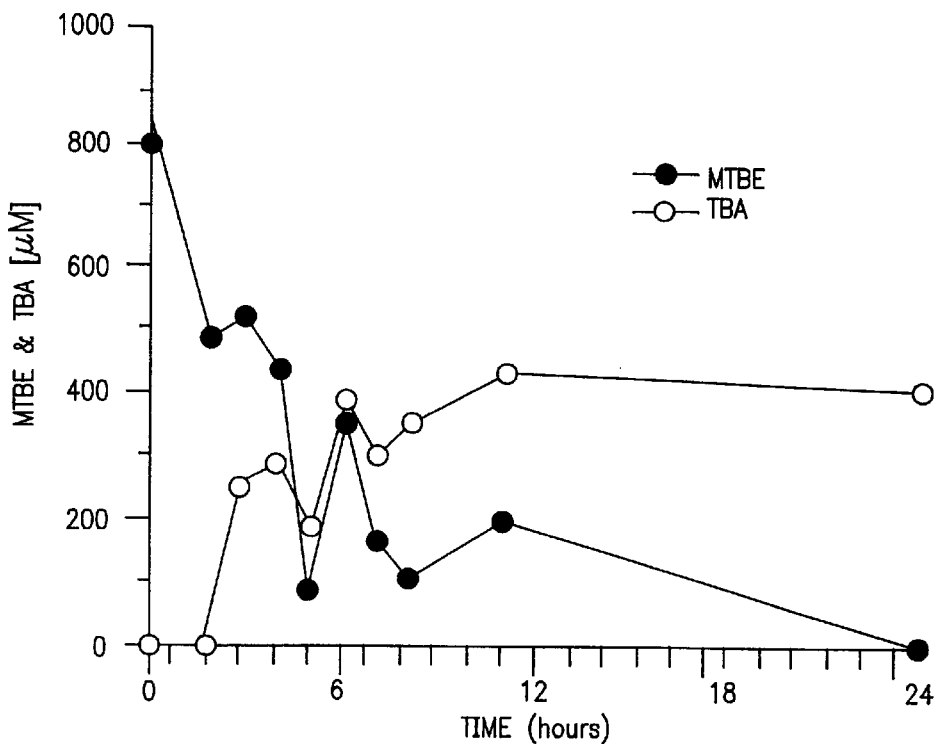
Figure 1B:
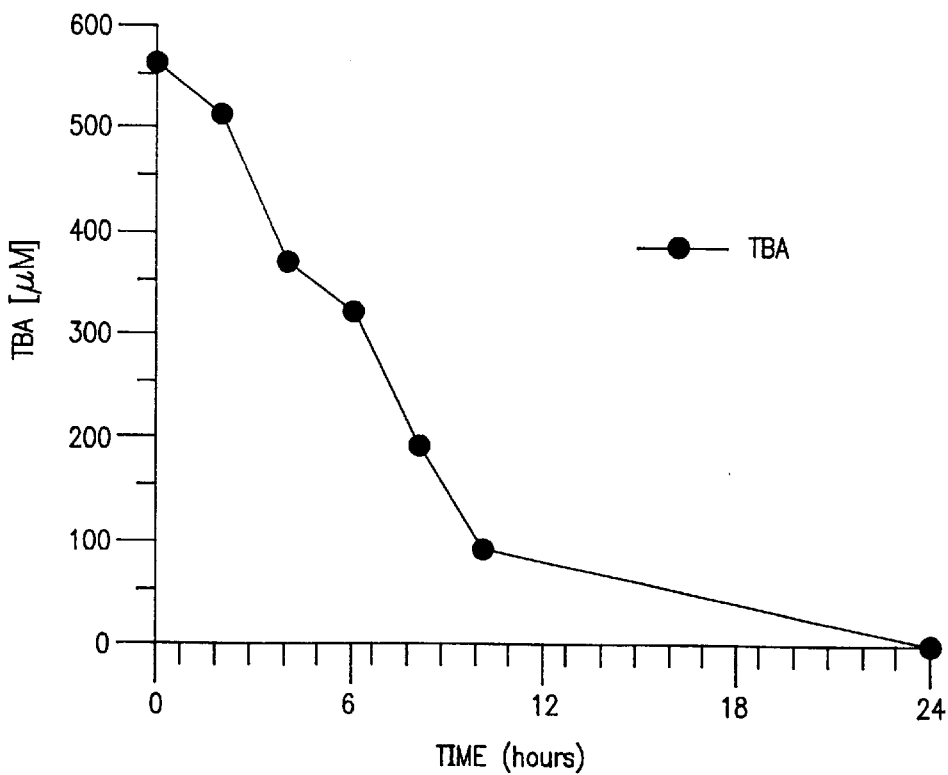

The present invention relates to a method for removing cells from the above-mentioned fermentation broth using a membrane, comprising adding polyethyleneimine to the fermentation broth to form a mixture, and then filtering the mixture through the membrane to separate the cells.

The method of the present invention can improve the permeation rate in removing cells from a fermentation broth using a membrane by from 1.5 to 4.0 times as compared to the case in which the treatment in the present invention is not conducted. This makes it possible to easily improve the membrane permeation rate without using large-sized equipment and to increase an efficiency of the membrane permeation equipment.

The microorganism belonging to the genus Escherichia which is used in the present invention may be a wild strain or a mutant. A recombinant strain which is derived through cell fusion or genetic manipulation is also available. An example of microorganisms belonging to the genus Escherichia is *Escherichia coli*. The desired product produced by this microorganism may be a product which is permeated through a UF membrane or an MF membrane which is used in the present invention. Examples thereof include amino acids such as lysine, glutamic acid, isoleucine, valine and leucine; nucleic acids such as inosine and guanosine; organic acids such as lactic acid and malic acid; and vitamins.

The fermentation broth which is used in the present invention can be prepared by culturing the above-mentioned microorganism in an appropriate medium. The medium is not particularly limited, and it may be an ordinary medium containing a carbon source, a nitrogen source, an inorganic ion and optionally an organic nutrient. The fermentation may be conducted by the method described in International Publication No. WO95/16042, Published European Patent Application No. 0685,555 or Japanese Laid-Open Patent Application (Kokai) No. 047,397/1996 under appropriate conditions for growth of the above-mentioned microorganism.

Any carbon source can be used so long as it is applicable to the above-mentioned microorganism. Specific examples of the carbon source include saccharide such as glucose, fructose, sucrose and maltose; organic acids such as fumaric acid, citric acid, acetic acid and propionic acid; and salts thereof.

Any nitrogen source can be used so long as it is applicable to the above-mentioned microorganism. Specific examples of the nitrogen source include inorganic acid ammonium salts such as ammonium sulfate and ammonium chloride; organic acid ammonium salts such as ammonium fumarate and ammonium citrate; nitric acid salts such as sodium nitrate and potassium nitrate; organic nitrogen compounds such as peptone, yeast extract, meat extract and corn steep liquor; and a mixture thereof.

A nutrient source which is used in ordinary fermentation may be used as required. Examples of the nutrient source include inorganic salts, trace metallic salts and vitamins.

In general, PEI can be obtained in the form of an aqueous solution. However, when PEI is added to an $E.$ $coli$ fermentation broth, it is advisable to add an aqueous solution containing from 1 to 50% of PEI, whereby an increase in the viscosity of the PEI aqueous solution is controlled and dilution of the fermentation broth is prevented. With respect to the addition of PEI, it is considered that a predetermined amount of a 10% PEI aqueous solution is added while the fermentation broth is stirred when the fermentation is completed. However, the method of the addition is not particularly limited so long as a uniform mixture can be obtained.

The amount of PEI added is between 0.0005 and 0.5% by weight, preferably between 0.001 and 0.05% by weight based on the $E.$ $coli$ fermentation broth.

PEI to be added may be water-soluble, and an average molecular weight thereof is not particularly limited. PEI having an average molecular weight of approximately from 10,000 to 100,000 is easy to obtain and to treat.

When the membrane separation is conducted after the addition of PEI, the membrane permeation rate can be improved. Further, when the pH of the $E.$ $coli$ fermentation broth after the addition of PEI is adjusted to from 3 to 9, preferably to from 4 to 7, the membrane permeation rate can be more improved. When the pH of the fermentation broth after the addition of PEI is nearly in a neutral region, there is no need to readjust the pH. However, when the pH is readjusted to the above-mentioned range, a higher membrane permeation rate can be obtained at times. Thus, the readjustment of the pH can be conducted as required.

An ordinary pH adjustor can be used to adjust the pH. Examples thereof include acids such as hydrochloric acid, sulfuric acid and phosphoric acid; and alkali compounds such as sodium hydroxide, potassium hydroxide and ammonia.

The fermentation broth may be heat-treated before or after the addition of PEI. An appropriate heat-treatment temperature is between 50° and 130° C., and an appropriate heat-treatment time is between 10 and 20 minutes. This heat-treatment can improve an efficiency of mixing PEI and a permeation rate.

The membrane to be used may be MF or UF. A flat membrane, a hollow fiber membrane, a tubular membrane or a spiral membrane is available. The material of the membrane may be an organic material such as polysulfone, polyolefin, polyvinylidene difluoride or Teflon, or an inorganic material such as a ceramic. In the case of UF, a membrane having a molecular weight cut off of from 1,000 to 500,000 is actually convenient. In the case of MF, a membrane having a pore diameter of from 0.05 to 1 $\mu$m is appropriate.

Having generally described this invention, a further understanding can be obtained by reference to certain specific examples which are provided herein for purposes of illustration only and are not intended to be limiting unless otherwise specified.

EXAMPLES

A test for membrane permeation in Example 1 and 2 was conducted by mounting two PTTK membranes (UF membranes made by Millipore, U.S.A., molecular weight cut off ; 30,000) on a Minitan module made by Millipore. Further, with respect to PEI, a 10% aqueous solution obtained by diluting with pure water a 50% PEI solution having an average molecular weight of 50,000 (made by Sigma) was used.

Example 1

L-lysine was produced by the method described in the Examples of International Publication No. WO95/16042 using B-399/RSFD80 strain obtained by introducing plasmid/RSFD80 into $E.$ $coli$ B-399 strain. The fermentation was conducted at a temperature of 37° C. for 48 hours using a medium having the following formulation while stirring the mixture at from 114 to 116 rpm.

Formulation of the medium for production of L-lysine:

| A: | $(NH_4)_2SO_4$ | 16 g/liter |
|---|---|---|
|  | $KH_2PO_4$ | 1 g/liter |
|  | $MgSO_4.7H_2O$ | 1 g/liter |
|  | $FeSO_4.7H_2O$ | 0.01 g/liter |
|  | $MnSO_4.5H_2O$ | 0.01 g/liter |
|  | yeast extract (Difco) | 2 g/liter |
|  | L-methionine | 0.5 g/liter |
|  | The pH was adjusted to 7.0 with KOH, and the mixture was autoclaved at 115° C. for 10 minutes (16/20 volume). | |
| B: | 20% glucose (which was autoclaved at 115° C. for 10 minutes) (4/20 volume) | |
| C: | $CaCO_3$ by Japanese pharmacopeia (which was sterilized with dry heat at 180° C. for 2 days) (30 g/liter) | |

(A and B were mixed at a ratio of 4:1, and C was added thereto in an amount of 30 g/liter. Antibiotics (100 $\mu$g/ml of streptomycin and 5 $\mu$g/ml of kanamycin) were added to the mixture. The obtained mixture was used as the medium for production of L-lysine.)

When the fermentation was completed, the concentration of L-lysine produced was 9.2 g/liter calculated as lysine hydrochloride.

To each 300 ml of the thus-obtained lysine fermentation broth was added the above-mentioned 10% PEI solution in an amount of 0.32 g, 0.91 g or 1.6 g. The mixture was adjusted to a pH of 4.0 with 98% sulfuric acid, and was heated at 60° C. for 20 minutes while being stirred. The concentrations of PEI in the fermentation broth after the addition of PEI in the above-mentioned amounts were approximately 100 ppm, 300 ppm and 500 ppm respectively.

The thus-treated fermentation broths were used in the test for membrane permeation. The test for membrane permeation was conducted by feeding each of the above-treated fermentation broths to the above-mentioned UF module at a rate of 1,000 ml/min while maintaining the fermentation broth at 50° C. and permeating it through the membrane at an average pressure of 0.9 kg-f/cm$^2$. The change in the permeation rate was measured over the course of the permeation time of 30 minutes. The results are shown in FIG. 1.

As is apparent from FIG. 1, in the case of the *E. coli* fermentation broth, the membrane permeation rate was abruptly decreased at the initial stage of the cell removal (within 5 minutes after the start-up), and was later gradually stable. Upon comparison of the respective permeation rates after 30 minutes, the permeation rate with the addition of PEI was at most 4 times as high as that with no addition of PEI. The improvement of the permeation rate was remarkably observed with the addition of 100 ppm of PEI, and the permeation rate in this case was twice as high as that with no addition of PEI.

Example 2

L-isoleucine was produced using *E. coli* AJ12919 strain described in Published European Patent Application No. 0685,555 or Japanese Laid-Open Patent Application (Kokai) No. 047,397/1996. AJ12919 strain was spread on a culture medium containing 1% bactotrypton, 0.5% yeast extract, 0.5% NaCl, 1.5% agar, 100 μg/ml of streptomycin and 100 μg/ml of ampicillin, and was incubated at 37° C. for from 18 to 24 hours. Then, a part of the broth was inoculated in 300 ml of a fermentation medium (containing 4% glucose, 1.6% ammonium sulfate, 0.1% potassium dihydrogen phosphate, 0.1% magnesium sulfate 7-hydrate, 0.001% ferrous sulfate 7-hydrate, 0.001% manganese sulfate 5-hydrate, 0.2% yeast extract and 3% calcium carbonate, pH 7.0) using a platinum loop, and was cultured at 37° C. for 16 hours with an air permeability of 300 ml/min while being stirred at 400 rpm to obtain a seed culture broth. The resulting seed culture broth was inoculated in a fermentation medium containing 6% glucose, 1.6% ammonium sulfate, 0.1% potassium dihydrogen phosphate, 0.1% magnesium sulfate 7-hydrate, 0.001% ferrous sulfate 7-hydrate, 0.001% manganese sulfate 5-hydrate and 0.2% yeast extract (pH 7.0). Glucose was fed in an appropriate amount at 37° C. with an air permeability of 300 ml/min while controlling the number of rotations such that the dissolved oxygen concentration in the medium reached 5% or more. The mixture was cultured for 23 hours while maintaining the pH at approximately 7.0 with an ammonia gas. When the fermentation was completed, the concentration of L-isoleucine accumulated was 37 g/liter.

The thus-obtained L-isoleucine fermentation broth was heated at 120° C. for 10 minutes when the fermentation was completed, and the pH was adjusted to 4.0 with hydrochloric acid. To 300 ml of the thus-treated fermentation broth were added 0.3 g of a 10% PEI solution, and the mixture was reheated at 60° C. for 20 minutes. A fermentation broth which was heated at 60° C. for 20 minutes with no addition of PEI was used as a control. The test for membrane permeation was conducted in the same manner as in Example 1. The results are shown in Table 1.

TABLE 1

| | Membrane permeation rate [liter/m$^2$ · hour · (kg − f/cm$^2$)] | |
|---|---|---|
| Permeation time (min) | No addition of PEI | Addition of PEI |
| 1 | 75 | 96 |
| 5 | 60 | 76 |
| 10 | 55 | 69 |
| 20 | 50 | 62 |
| 30 | 48 | 58 |

As is clear from Table 1, the membrane permeation rate was increased with the addition of 100 ppm of PEI in the case of the isoleucine fermentation broth as well.

Example 3

*E. coli* FERM-P 5274 strain which belonged to the genus Escherichia, was resistant to β-2-thienyl-alanine and had an ability to produce L-leucine(disclosed in Japanese Laid-Open Patent Application (kokai) No. 34,397/1987) was subjected to a mutation treatment with N-methyl-N'-nitro-N-nitrosoguanigine. Out of the mutated strains, a strain which was resistant to 4-azaleucine was isolated to obtain a strain having an improved ability to produce L-leucine.

The thus-obtained strain was cultured at 31° C. for 72 hours with stirring in a medium (containing 5 g/dl glucose, $(NH_4)_2SO_4$ 2.5 g/dl, $KH_2PO_4$ 0.2 g/dl, $MgSO_4$ 7H2O 0.1 g/dl, yeast extract 0.05 g/dl, thiamine hydrochloride 1 mg/L, $FeSO_4 \cdot 7H_2O$ 1 mg/dl, $MnSO_4 \cdot 4H_2O$ 1 mg/dl, $CaCO_3$ 2.5 g/dl, pH 7.0). When the fermentation was completed, the concentration of L-leucine accumulated was 3.1 g/dl.

The above-mentioned 10% PEI solution was added to each 300 ml of the thus-obtained fermentation broth to prepare the fermentation broth having the PEI concentration of 0, 200 and 1000 ppm respectively. The obtained broth was adjusted to a pH of 4.0 with 98% sulfuric acid and was heated at 60° C. for 30 minutes while being stirred.

The thus-treated broths were used in the test for membrane permeation. The test for membrane permeation was conducted by feeding each of the above-treated broths to Pencil type PSP-003 module (pore diameter; 0.3 μm, membrane area; 150 cm$^2$) made by Asahi Chemical Industry Co., Ltd. at a rate of 600 ml/min at an entrance pressure of 1.0 kg-f/cm$^2$. The change of the permeation rate was measured over the course of the time of 60 minutes.

The results are shown in FIG. 2. As is apparent from FIG. 2, the membrane permeation rate was increased with the addition of PEI in case of L-leucine fermentation broth as well.

The disclosure of Japan priority patent application No. 265275/1995, filed Oct. 13, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for improving the permeation rate of an Escherichia cell-containing fermentation broth through a microfiltration or an ultrafiltration membrane consisting of adding an effective amount of polyethyleneimine to the fermentation broth to form a mixture, adjusting the pH of the mixture to from 3 to 7, heating the mixture to from 50° C. to 130° C. and then filtering the mixture through a microfiltration or an ultrafiltration membrane to separate the cells.

2. A method for improving the permeation rate of an Escherichia cell-containing fermentation broth through a microfiltration or an ultrafiltration membrane consisting of heating the fermentation broth to from 50° C. to 130° C., adding an effective amount of polyethyleneimine to the fermentation broth to form a mixture, adjusting the pH of the mixture to from 3 to 7, and then filtering the mixture through either a microfiltration or an ultrafiltration membrane to separate the cells.

3. The method of claim 1, wherein the amount of the added polyethyleneimine is between 0.0005 and 0.5% by weight based on the fermentation broth.

4. The method of claim 2, wherein the amount of the added polyethyleneimine is between 0.0005 and 0.5% by weight based on the fermentation broth.

5. The method of claim 1, wherein the molecular weight of the polyethyleneimine is 10,000 to 100,000.

6. The method of claim 1, wherein the amount of the added polyethyleneimine is between 0.001 and 0.05% by weight based on the fermentation broth.

7. The method of claim 2, wherein the molecular weight of the polyethyleneimine is 10,000 to 100,000.

8. The method of claim 2, wherein the amount of the added polyethyleneimine is between 0.001 and 0.05% by weight based on the fermentation broth.

* * * * *